United States Patent [19]

Trumble et al.

[11] Patent Number: 4,847,002

[45] Date of Patent: Jul. 11, 1989

[54] IMPROVED STABILIZATION OF WOOD PRESERVATIVE SOLUTIONS AND PRESERVATION OF WOOD BY SUCH SOLUTIONS

[75] Inventors: William P. Trumble, Kanata; Cheryl M. Maritan, Ottawa, both of Canada

[73] Assignee: Bell Canada, Montreal, Canada

[21] Appl. No.: 86,240

[22] Filed: Aug. 14, 1987

Related U.S. Application Data

[63] Continuation of Ser. No. 832,878, Feb. 26, 1986, abandoned.

[30] Foreign Application Priority Data

Nov. 25, 1985 [CA] Canada .................................. 496099

[51] Int. Cl.[4] ...................... C09K 15/32; C09K 15/06; A01N 59/20; A61K 33/34

[52] U.S. Cl. .............................. 252/400.5; 106/15.05; 106/18.28; 162/160; 162/161; 162/181.4; 162/181.5; 252/400.53; 252/400.54; 252/400.61; 252/400.62; 252/407; 252/602; 252/607; 424/623; 424/626; 427/297; 427/325; 427/440; 428/537.1; 428/541; 428/907

[58] Field of Search .................. 252/400.1, 400.5, 607, 252/602, 400.53, 400.54, 400.61, 400.62, 407; 106/15.05, 18.36, 18.28, 18.26; 427/439, 440, 351, 370, 305, 317, 297, 419.2, 325, 440; 428/541, 537.1, 907; 424/140, 137, 133, 134, 141, 151, DIG. 11; 162/158, 160–161, 181.4, 181.5

[56] References Cited

U.S. PATENT DOCUMENTS

| | | | |
|---|---|---|---|
| 3,957,494 | 5/1976 | Oberley | 106/15.05 |
| 4,218,249 | 8/1980 | Hill | 427/440 |
| 4,247,329 | 1/1981 | Mills | 427/440 |
| 4,303,705 | 12/1981 | Kelso, Jr. | 427/440 |
| 4,323,477 | 4/1982 | Hill | 252/397 |
| 4,325,993 | 4/1982 | Schroder | 427/440 |
| 4,466,998 | 8/1984 | McIntyre et al. | 427/440 |
| 4,567,115 | 1/1986 | Trumble | 428/541 |
| 4,656,060 | 4/1987 | Krzyzewski | 427/441 |

FOREIGN PATENT DOCUMENTS

| | | |
|---|---|---|
| 10991/70 | 2/1980 | Australia . |
| 31578/77 | 2/1980 | Australia . |
| 1187255 | 8/1971 | Canada . |
| 1959993 | 8/1970 | Fed. Rep. of Germany . |
| 226975 | 8/1971 | Fed. Rep. of Germany . |
| 1137502 | 5/1951 | France . |
| 1475476 | 2/1967 | France . |
| 145204 | 2/1931 | Switzerland . |
| 468873 | 4/1969 | Switzerland . |
| 756685 | 9/1956 | United Kingdom . |
| 1023465 | 5/1966 | United Kingdom . |

OTHER PUBLICATIONS

"Wood Technology Enhances Pole Line Reliability", Telephony, J. Ochrymowych, Sep. 2, 1985, pp. 30–32, 36, 72, 76 & 80.

"Wood Preservation", B. A. Richardson, The Construction Press, pp. 69 & 164.

"Fluoro-Chrome-Arsenate-Phenol[1]", American National Standards Institute, pp. 276–278, 280, 538 and 539.

"Wood Deterioration and its Prevention by Preservative Treatments", Nicholas, vol. II, p. 246, Syracuse U. Press.

Advertisement, Entitled "Lanthology", Molycorp. Inc., White Plains, N.Y.

Hawley, G., 1981, The Condensed Chemical Dictionary, 10th Edition, Van Nostrand Reinhold Co., New York., p. 940.

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A wood preservative solution comprising water, hexavalent chromium, copper and arsenic can be stabilized against precipitation by the addition of fluorine ion, thereby enhancing the useful life and safety of the solution. Fluoride salts like cerium fluoride, sodium fluoride and calcium fluoride are suitable sources for fluorine ion in such a solution. Wood treated with the preservative solution displays increased penetration, distribution and retention of chromium, copper and arsenic.

53 Claims, No Drawings

IMPROVED STABILIZATION OF WOOD PRESERVATIVE SOLUTIONS AND PRESERVATION OF WOOD BY SUCH SOLUTIONS

This application is a continuation of application Ser. No. 832,878, filed Feb. 26, 1986 now abandoned.

BACKGROUND OF THE INVENTION

This invention relates to the stabilization of wood preservative solutions, particularly those solutions containing chromium, copper and arsenic, and to the preservation of wood by such stabilized solutions.

The chromium/copper/arsenate solutions, generally referred to as CCA preservatives, are very widely used to preserve wood against the action of fungi. During storage as well as actual use, the chromium, copper and arsenic salts in CCA solutions tend to precipitate, due in part to the effect of extractants from the wood and other reducing contaminants. This precipitation limits the useful life of CCA solutions and also produces residual precipitates that require special treatment and storage because of their harmful effects on people and the environment.

SUMMARY OF THE INVENTION

The present invention involves the use of an additive that improves the stability of CCA solutions by reducing the rate of salt precipitation. This improvement reduces the cost of storage and disposal of spent solutions as the useful life of the solution is increased. The present invention also reduces the consumption of chromium, copper and arsenic oxides used to replace those lost by precipitation. There is, moreover, a reduction achieved with the present invention in the volume of residual materials that need to be stored and treated, reducing the risk of exposure by the public. The additive also improves the pilodyne penetration of the wood.

In achieving these improvements, the present invention provides a wood preservative solution comprising water, hexavalent chromium, copper, arsenic and an amount of fluorine ion sufficient to stabilize the solution against precipitation of at least the chromium. In accordance with another aspect of the present invention, there is also provided a method for treating wood with the aforesaid wood preservative solution. In a preferred embodiment, the wood preservative solution comprises (1) water, (2) about 2 to 3.0% concentration of chromium, copper and arsenic salts or oxides, (3) about 0.5% to 10% concentration of a polyethylene glycol having a molecular weight of about 1,000, and (4) between about 0.001 and 0.4% of a fluoride salt contributing the fluorine ion to the solution.

Also provided, in accordance with yet another aspect of the present invention, is an article of manufacture produced by a process comprising the step of treating wood with a wood preservative solution comprising water, hexavalent chromium, copper, arsenic and an amount of fluorine ion sufficient to stabilize said solution aginast precipitation of said chromium, said copper, and said arsenic. In one preferred embodiment, the wood thus treated comprises sapwood into which said solution penetrates substantially completely.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

In accordance with the present invention, the stability of CCA solutions is improved by the addition thereto of a source of fluorine ion, such as a fluoride salt. A preferred fluoride is cerium fluoride ($CeF_3$), although other fluorides, such as Na, Cm and Ca fluoride salts, can be used. The amount of fluoride salt added is preferably slightly more than the solubility limit of the particular salt.

The standard CCA solution is specified in ASTM standard D1625-71, and the preferred example thereof is Type C, identified "CCA-C." The CCA-C formulation is as follows: hexavalent chromium, calculated as $CrO_3$, 44.5-50.5%; bivalent copper, calculated as CuO, 17.0-21.0%; pentavalent arsenic, calculated as $As_2O_5$, 30.0-38.0%. The nominal composition is considered to be 47.5% $CrO_3$, 18.5% CuO and 34% $As_2O_5$. The basic CCA-C standard solution, which is well known and widely used, is normally diluted by the addition of 40 to 50 parts of water to one part of basic solution, thereby providing a 2% - 3% (preferably about 2.5%) aqueous solution.

A modification of the CCA-C standard solution is described in U.S. application Ser. No. 635,868, filed July 30, 1984, the contents of which are hereby incorporated by reference. The modified solution contains a polymer of ethylene glycol (PEG). The PEG additive operates to reduce the surface-hardening effect of the standard solution. A preferred embodiment of the modified solution is obtained by adding to the standard CCA-C formulation PEG in the molecular weight range of about 100 to 2,000, in particular 500 to 2,000 and more particularly 1,000. The PEG is added to the water-based CCA solution slowly and steadily, to a concentration of between about 0.5 to 10%, with the solution preferably remaining below about 85° F., more particularly between about 70° and 85° F., during the process. The pH is preferably kept below 2.0, in particular between about 1.7 and 2.0.

In accordance with the present invention, it is preferred that a flouride salt is added either to a CCA-C solution or to a CCA-C solution modified by the addition of PEG. The particular fluoride salts used are selected by their solubility in the respective solutions. Salts of limited solubility are desired for at least two reasons. First, an excessive increase in the amount of dissolved fluoride salt has an effect on the electrical conductivity of the treated wood, which is undesirable for poles used for supporting power lines and telephone lines. For wood not used in situations where the conductivity is critical, higher levels of fluoride salt can be used, so long as the total amount of $F^-$ in the final solution is not sufficient to retard the conversion of hexavalent chromium to trivalent in the wood matrix, after application of the solution and penetration into the matrix of the ionic constituents. A further feature, that of using the lower levels of fluoride salt, avoids the need for a substantial change to the solution formulation and, thereby, for extensive use-approval testing.

As noted above, it is preferred that the percentage of fluoride salt added to a preservative solution within the present invention be approximately equal to the solubility of the salt in the solution. As an example, the solubility of $CeF_3$ is less than 0.4%. With a level of $CeF_3$ of 0.4%, there is an excess of $CeF_3$. Lower levels of $CeF_3$ are suitable, however. Other fluoride-containing compounds with limited solubility in the standard solutions also provide improved stability. The low solubility precludes the build-up of soluble fluorides in the solution, and thus minimizes the salt effect of increasing the electrical conductivity of the wood.

The solutions listed in Table 1 are examples only, and are indicative of the effect of adding a fluorine salt to a treatment solution as described above. To illustrate the effect of extractants and other contaminants, chromium-reducing sugar was added to standard preservative solutions containing a fluoride salt. The proportions reported below are by weight, and the various additives (that is, fluorine salt and sugar where used, were added to the original solution of CCA-C or CCA-C/PEG (taken as 100%). For each solution, the times are given (in hours) for a particular level of precipitation to occur with (B) and without (A) the fluoride salt, respectively. As a general indication of the enhancement in stability achieved with the present invention, the percentage improvement (C), calculated as $[(B-A)/A]\times 100$, is also given.

TABLE 1

| | A | B | C* |
|---|---|---|---|
| 2.5% CCA-C + 0.4% $CeF_3$ + 10% Sugar | 38 | 49 | 26 |
| 2.5% CCA-C-C/10% PEG + 0.4% $CeF_3$ | 60 | 90 | 50 |
| 2.5% CCA-C/4% PEG + 0.4% $CeF_3$; | 220 | 336 | 53 |
| 2.5% CCA-C + 0.4% $CeF_3$ + 5% sugar | 56 | 77 | 37.5 |
| 2.5% CCA-C + 0.01% $CeF_3$ + 10% sugar | 38 | 50 | 31.5 |
| 2.5% CCA-C + 0.01% $CeF_3$ + 5% sugar | 55 | 77 | 40 |
| 2.5% CCA-C + 0.01% NaF + 5% sugar | 55 | 71 | 29 |
| 2.5% CCA-C + 0.01% NaF + 10% sugar | 38 | 47 | 23.5 |
| 2.5% CCA-C + 0.05% NaF + 5% sugar | 55 | 74 | 34.5 |
| 2.5% CCA-C + 0.05% NaF + 10% sugar | 38 | 51 | 34 |
| 2.5% CCA-C + 0.1% NaF + 10% sugar | 38 | 55 | 45 |
| 2.5% CCA-C + 0.2% NaF + 10% sugar | 38 | 61 | 60 |
| 2.5% CCA-C + 0.01% $CaF_2$ + 5% sugar | 55 | 69 | 25.5 |
| 2.5% CCA-C + 0.01% $CaF_2$ + 10% sugar | 38 | 47 | 23.5 |

*A = Precipitation without flourine salt
B = Precipitation with flourine salt
C = Approximate % improvement The particular salts exemplified in Table 1 represent the various forms suitable for use in the present invention. Cerium fluoride thus exemplifies the rare earth fluorides, calcium fluoride the alkaline earth fluorides, and sodium fluoride the alkaline metal fluorides. Calcium fluoride and sodium fluoride were chosen as exemplary because of ready supply and low cost, being among the more attractive fluorides for these reasons. Cerium fluoride was likewise selected because it is readily available and relatively inexpensive. However, other fluorides of the exemplified groups -- rare earth fluorides, alkaline earth fluorides, alkaline metal fluorides—can be used.

As described in the above-mentioned U.S. patent application, standard CCA solutions cause hardening of the outer portion of wood treated with the standard solutions. Such hardening is a serious effect in utility poles, in that service personnel who climb the poles experience difficulty in obtaining a secure grip by the spurs on their climbing boots. The addition of fluoride salt at least partly mitigates this hardening effect.

However, improvement in the pilodyne penetration of wood treated in accordance with the present invention is obtained. (The pilodyne penetration relates to a test in which a spike having a particular shape is pushed into the wood under a predetermined load, the penetration of the spike being measured.) As an example, for wood treated with a standard CCA-C solution, average penetration was 14.8 mm; for wood treated with a CCA-C/fluoride solution, average penetration was 16.8 mm; and for wood treated with CCA-C/PEG/fluoride solution, the average penetration was 19.6 mm.

In addition to improving the stability of preservation solutions by reducing precipitation as described above, the present invention also provides an increase in gross absorption, penetration, distribution and retention in the wood of the chromium, copper and arsenic ions from such solutions. This effect enhances the fungicidal effect by placing these ions more deeply within the matrix of the wood.

The test results enumerated in Table 2 are indicative of penetration into and retention by red pine of the various ionic species from preservative solutions applied to the wood. From both of red pine, each about four feet long, core samples were obtained by boring radially into each bolt with a hollow drill. See Ochrymowych, "The art of wood preservation: Enhancing pole line reliability," *Telephony, Sept.* 16, 1985, at 72–80, the contents of which are hereby incorporated by reference. Prior to the core-sampling operation, Bolt No. 1 was treated with 2.5% CCA-C solution, Bolt No. 2 with 2.5% CCA-C solution containing 0.05% $CeF_3$, and Bolt No. 3 with 2.5% CCA-C solution containing 4.0% DEG and and 0.05% $CeF_3$. Each core sample was divided along its length into 10 mm segments, each of which was then ground (40 mesh particle size) and subjected to elemental analysis of energy dispersive x-ray spectrometry. Thus, each 10-mm segment represented a different "assay zone" along a radial directed into the treated wood.

It will be seen from the data in Table 2 that enhanced penetration and retention was achieved when a fluoride salt was added, in accordance with the present invention, compared to solutions lacking fluorine ion.

The physical basis for the stabilization effect achieved with the present invention is not fully understood. It is thought, however, that the above-described improvements are related to the formation of complexes, by electrostatic interaction or hydrogen bonding, between $F^-$ and $Cr^{(vi)}$ in solution, thereby stabilizing the chromium against precipitation.

TABLE 2

| Bolt No. | Thickness of Sapwood (mm) | Depth of Penetration | Percentage Penetration Through Sapwood | Assay Zone (mm) | Preservative Retention (kg/m$^3$) Cr | Cu | As | Total |
|---|---|---|---|---|---|---|---|---|
| 1 | 70 | 62 | 90% | 0–10 | 12.4 | 3.6 | 7.1 | 23.1 |
| | | | | 10–20 | 7.8 | 3.1 | 6.4 | 17.3 |
| | | | | 20–30 | 6.7 | 3.0 | 6.2 | 15.9 |
| | | | | 30–40 | 5.2 | 2.8 | 5.8 | 13.8 |
| | | | | 40–50 | 3.4 | 2.1 | 4.4 | 9.9 |
| 2 | 63.5 | 63.3 | 100% (approx.) | 0–10 | 12.7 | 3.5 | 7.1 | 23.3 |

TABLE 2-continued

| Bolt No. | Thickness of Sapwood (mm) | Depth of Penetration | Percentage Penetration Through Sapwood | Assay Zone (mm) | Preservative Retention ($kg/m^3$) Cr | Cu | As | Total |
|---|---|---|---|---|---|---|---|---|
| | | | | 10-20 | 8.4 | 3.2 | 6.8 | 18.4 |
| | | | | 20-30 | 6.5 | 2.9 | 6.6 | 16.0 |
| | | | | 30-40 | 5.4 | 2.8 | 6.4 | 14.6 |
| | | | | 40-50 | 4.1 | 2.3 | 5.2 | 11.6 |
| 3 | 57.2 | 59.3 | >100% | 0-10 | 12.2 | 3.4 | 6.5 | 22.1 |
| | | | | 10-20 | 9.0 | 3.3 | 7.5 | 19.8 |
| | | | | 20-30 | 6.7 | 3.0 | 7.1 | 16.8 |
| | | | | 30-40 | 5.7 | 2.8 | 6.5 | 15.0 |
| | | | | 40-50 | 4.4 | 2.2 | 5.4 | 12.0 |

*Penetration beyond porous sapwood into denser heartwood observed.

What is claimed is:

1. An aqueous wood preservative solution comprising a CCA-type formulation consisting essentially of 33% to 69.3% hexavalent chromium, calculated as $Cr_2O_3$; 16% to 22% bivalent copper, calculated as CuO; and 14.7% to 48% pentavalent arsenic, calculated as $As_2O_5$; diluted with water, and an amount of $F^-$ ion sufficient to stabilize said solution against precipitation of at least said chromium without retarding conversion of hexavalent chromium to trivalent chromium in a wood matrix.

2. A wood preservative solution according to claim 1, wherein said fluorine ion is contributed by a fluoride salt added to said solution.

3. A wood preservative solution according to claim 2, wherein said preservative solution is the produce of a process comprising the step of diluting a Type C standard CCA solution, as specified in ASTM standard D1625-71, with water to form a 2 to 3% aqueous solution of said standard CCA solution.

4. A wood preservative solution according to claim 2, wherein said fluoride salt is at least one selected from the group consisting of a rare earth fluoride, an alkaline earth fluoride and an alkaline metal fluoride.

5. A wood preservative solution according to claim 4, wherein said fluoride salt is selected from the group consisting of cerium fluoride, sodium fluoride and calcium fluoride.

6. A wood preservative solution according to claim 1, further consisting essentially of polyethylene glycol.

7. A wood preservative solution according to claim 6, wherein said polyethylene glycol has a molecular weight in the range from about 100 to about 2,000.

8. A wood preservative solution according to claim 7, wherein said molecular weight range of said polyethylene glycol is from about 500 to about 2,000.

9. A wood preservative solution according to claim 6, wherein said preservative solution comprises (1) water, (2) about 2 to 3.0% concentration of chromium, copper and arsenic salts or oxides (3) about 0.5% to 10% concentration of a polyethylene glycol having a molecular weight of about 1,000, and (4) between about 0.001 and 0.4% of a fluoride salt contributing said fluorine ion to said solution.

10. A wood preservative solution according to claim 1, wherein said preservative solution has a pH below about 2.0 and a temperature below about 85° F.%.

11. A wood preservative solution according to claim 10, wherein said preservative solution has a pH between about 1.7 and 2.0 and a temperature between about 70° and 85° F.

12. A method of treating wood, comprising the step of exposing wood to an aqueous wood preservative solution comprising a CCA-type formulation consisting essentially of 33% to 69.3% hexavalent chromium, calculated as $Cr_2O_3$; 16% to 22% bivalent copper, calculated as CuO; and 14.7% to 48% pentavalent arsenic, calculated as $As_2O_5$; diluted with water, and an amount of $F^-$ ion sufficient to stabilize said preservative solution against precipitation of at least said chromium and insufficient to retard the conversion of hexavalent chromium to trivalent chromiumin a wood matrix.

13. A method according to claim 12, wherein said fluorine ion is contributed by a fluorine salt added to said solution.

14. A method according to claim 13, wherein said preservative solution is the product of a process comprising the step of diluting a Type C standard CCA solution, as a specified in ASTM standard D1625-71, with water to form a 2% to 3% aqueous solution of said standard CCA solution.

15. A method according to claim 13, wherein said fluoride salt is at least one selected from the group consisting of a rare earth fluoride, an alkaline earth fluoride and an alkaline metal fluoride.

16. A method according to claim 15, wherein said fluoride salt is selected from the group consisting of cerium fluoride, sodium fluoride and calcium fluoride.

17. A method according to claim 12, wherein said preservative solution further consists essentially of polyethylene glycol.

18. A method according to claim 17, wherein said polyethylene glycol has a molecular weight in the range from about 100 to about 2,000.

19. A method according to claim 18, wherein said preservative molecular weight range of said polyethylene glycol is from about 500 to about 2,000.

20. A method according to claim 17, wherein said preservative solution comprises (1) water, (2) about 2 to 3.0% concentration of chromium, copper and arsenic salts or oxides, (3) about 0.5% to 10% concentration of a polyethylene glycol having a molecular weight of about 1,000 and (4) between about 0.001 and 0.4% of a fluoride salt contributing said fluorine ion to said solution.

21. A method according to claim 12, wherein said preservative solution has a pH below about 2.0 and a temperature below about 85° F.

22. A method according to claim 21, wherein said preservative solution has a pH between about 1.7 and 2.0 and a temperature between about 70° and 85° F.

23. An article of manufacture produced by a process comprising the step of treating wood with a wood preservative solution comprising a CCA-type formulation consisting essentially of 33% to 69.3% hexavalent chromium, calculated as $Cr_2O_3$; 16% to 22% bivalent copper, calculated as CuO; and 14.7% to 48% pentavalent arsenic, calculated as $As_2O_5$; diluted with water, and an amount of $F^-$ ion sufficient to stabilize said preservative solution against precipitation of at least said chromium without retarding conversion of hexavalent chromium to trivalent chromium in a wood matrix.

24. An article according to claim 23, wherein said wood comprises sapwood into which said preservative solution penetrates substantially completely.

25. An article according to claim 23, wherein said fluorine ion is contributed by a fluoride salt added to said preservative solution.

26. An article according to claim 25, wherein said preservative solution is the product of a process comprising the step of diluting a Type C standard CCA solution, as specified in ASTM standard D1625-71, with water to form a 2 to 3% aqueous solution of said standard CCA solution.

27. An article according to claim 25, wherein said fluoride salt is at least one selected from the group consisting of a rare earth fluoride, an alkaline earth fluoride and an alkaline metal fluoride.

28. An article according to claim 27, wherein said fluoride salt is selected from the group consisting of cerium fluoride, sodium fluoride and calcium fluoride.

29. An article according to claim 23, wherein said preservative solution further consists essentially of polyethylene glycol.

30. An article according to claim 29, wherein said polyethylene glycol has a molecular weight in the range from about 100 to about 2,000.

31. An article according to claim 30, wherein said molecular weight range of said polyethylene glycol is from about 500 to about 2,000.

32. An article according to claim 29, wherein said preservative solution comprises (1) water, (2) about 2 to 3.0% concentration of chromium, copper and arsenic salts or oxides, (3) about 0.5% to 10% concentration of a polyethylene glycol having a molecular weight of about 1,000, and (4) between about 0.001 and 0.4% of a fluoride salt contributing said fluorine ion to said solution.

33. An article according to claim 23 wherein said preservative solution has a pH below about 2.0 and a temperature below about 85° F.

34. An article according to claim 33, wherein said preservative solution has a pH between about 1.7 and 2.0 and a temperature between about 70° and 85° F.

35. A method for stabilizing a wood preservative solution comprising a CCA-type formulation consisting essentially of 33% to 69.3% hexavalent chromium, calculated as $Cr_2O_3$; 16% to 22% bivalent copper, calculated as CuO; and 14.7% to 48% pentavalent arsenic, calculated as $As_2O_5$; diluted with water, comprising the step of adding a source of $F^-$ ion to said preservative solution in an amount sufficient to stabilize said preservative solution against precipitation of at least said chromium.

36. A method as claimed in claim 35, wherein said source of fluoride ion comprises a flouride salt.

37. A method as claimed in claim 36, wherein said fluoride salt has a low solubility in said preservative solution.

38. A method as claimed in claim 37, wherein said fluoride salt is added to said preservative solution in an amount approximately equal to the solubility of said fluoride salt in said preservative solution.

39. A method as claimed in claim 36, wherein said fluoride salt is at least one selected from the group consisting of a rare earth fluoride, an alkaline earth fluoride and an alkaline metal fluoride.

40. A method as claimed in claim 39, wherein said fluoride salt is selected from the group consisting of cerium fluoride, sodium fluoride and calcium fluoride.

41. A method as claimed in claim 35, wherein said preservative solution is a product of a process comprising the step of diluting a Type C standard CCA solution, as specified in ASTM standard D1625-71, with water to form a 2 to 3% aqueous solution of said standard CCA solution.

42. A method as claimed in claim 35, wherein said preservative solution further consists essentially of polyethylene glycol.

43. A method as claimed in claim 42, wherein said polyethylene glycol has a molecular weight in the range of from about 100 to about 2000.

44. A method as claimed in claim 41, wherein said aqueous solution further comprises polyethylene glycol.

45. A method as claimed in claim 44, wherein said polyethylene glycol is present at a concentration between 0.5 and 10%.

46. A method as claimed in claim 41, wherein said source of fluoride ion comprises a fluoride salt.

47. A method as claimed in claim 46, wherein said fluoride salt is at least one selected from the group consisting of a rare earth fluoride, an alkaline earth fluoride and an alkaline metal fluoride.

48. A method as claimed in claim 47, wherein said fluoride salt is at least one from the group consisting of cerium fluoride, sodium fluoride and calcium fluoride.

49. A method as claimed in claim 48, wherein said fluoride salt is cerium fluoride which is present in concentration up to about 0.4%.

50. A method as claimed in claim 42, wherein said source of fluoride ion comprises a fluorine salt.

51. A method as claimed in claim 50, wherein said fluoride salt is at least one selected from the group consisting of a rare earth fluoride, an alkaline earth fluoride and an alkaline metal fluoride.

52. A method as claimed in claim 51, wherein said fluoride salt is at least one from the group consisting of cerium fluoride, sodium fluoride and calcium fluoride.

53. A method as claimed in claim 52, wherein said fluoride salt is cerium fluoride which is present in a concentration up to about 0.4%.

* * * * *